(12) United States Patent
Nakamura et al.

(10) Patent No.: US 8,803,405 B2
(45) Date of Patent: Aug. 12, 2014

(54) ULTRASONIC TRANSDUCER, BIOLOGICAL SENSOR, AND METHOD FOR MANUFACTURING AN ULTRASONIC TRANSDUCER

(75) Inventors: Tomoaki Nakamura, Nagano (JP); Hironori Suzuki, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 24 days.

(21) Appl. No.: 13/479,937

(22) Filed: May 24, 2012

(65) Prior Publication Data

US 2012/0306316 A1     Dec. 6, 2012

(30) Foreign Application Priority Data

May 31, 2011    (JP) .................................. 2011-122158

(51) Int. Cl.
*H01L 41/08*     (2006.01)

(52) U.S. Cl.
USPC .......................................... 310/334; 310/324

(58) Field of Classification Search
USPC ............................................... 310/324, 334
See application file for complete search history.

(56) References Cited

U.S. PATENT DOCUMENTS

| | | | |
|---|---|---|---|
| 6,345,887 B1 * | 2/2002 | Sato ................................ | 347/72 |
| 7,401,525 B2 | 7/2008 | Cobianu et al. | |
| 2003/0206218 A1 * | 11/2003 | Miyata et al. .................. | 347/70 |

FOREIGN PATENT DOCUMENTS

| | | |
|---|---|---|
| JP | 10-135528 A | 5/1998 |
| JP | 2003-304595 A | 10/2003 |
| JP | 2006-051105 A | 2/2006 |
| JP | 2007-192649 A | 8/2007 |
| JP | 2008-536110 A | 9/2008 |
| JP | 2011-099675 A | 5/2011 |

OTHER PUBLICATIONS

3M Wafer Support System, Production Proven—Temporary wafer bonding for advanced IC packaging; 3M Company, Issued Dec. 2009, 4 pages.

\* cited by examiner

*Primary Examiner* — Mark Budd
(74) *Attorney, Agent, or Firm* — Global IP Counselors, LLP

(57) ABSTRACT

An ultrasonic transducer includes a resin substrate, a support film and a piezoelectric element. The resin substrate has an opening. The support film blocks off the opening in the resin substrate. The piezoelectric element is disposed on the support film in a region that blocks off the opening in plan view from a thickness direction of the support film. The piezoelectric element includes a lamination of a lower electrode, a piezoelectric body, and an upper electrode.

5 Claims, 7 Drawing Sheets

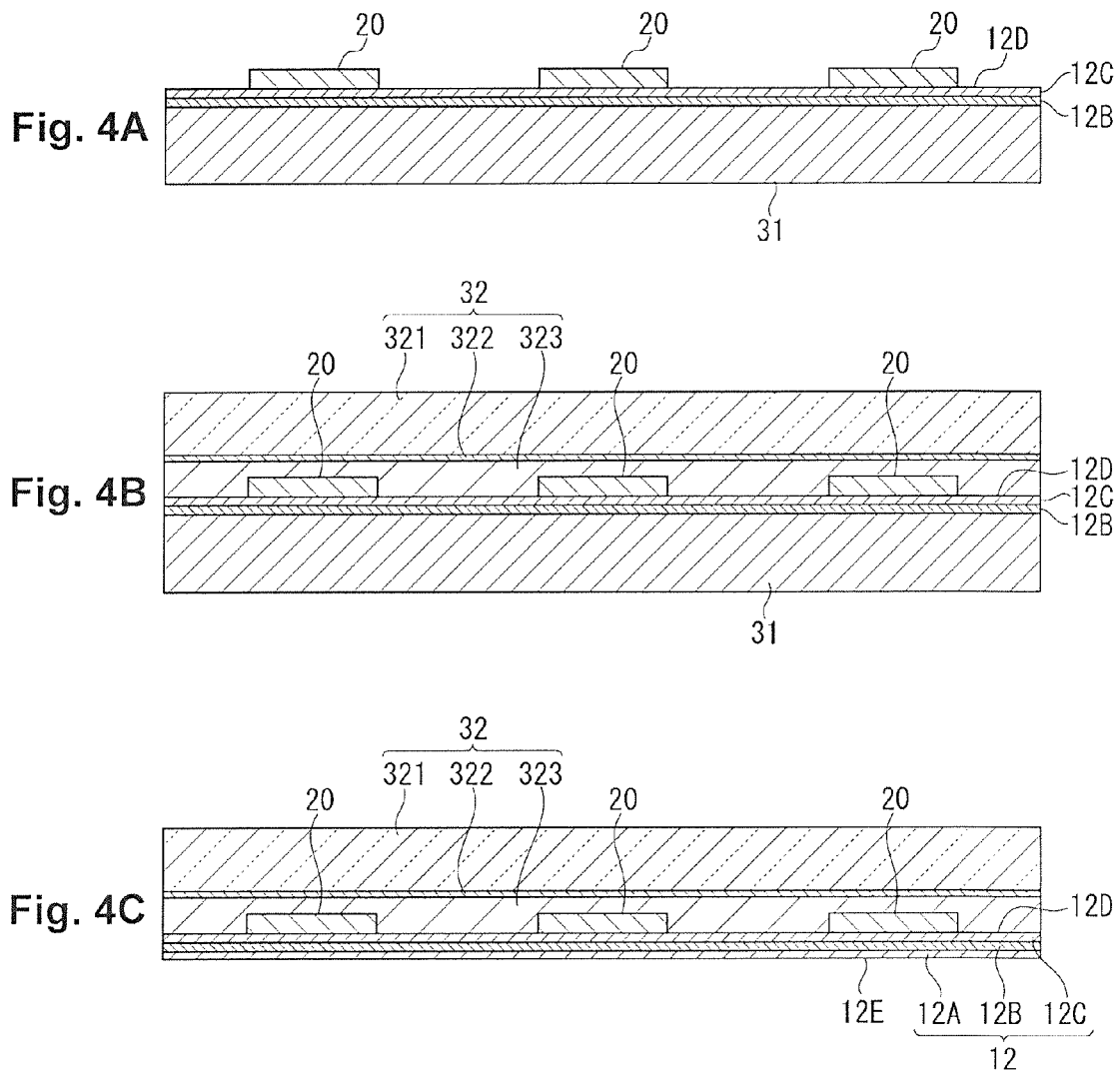

ULTRASONIC TRANSDUCER, BIOLOGICAL SENSOR, AND METHOD FOR MANUFACTURING AN ULTRASONIC TRANSDUCER

CROSS-REFERENCE TO RELATED APPLICATIONS

This application claims priority to Japanese Patent Application No. 2011-122158 filed on May 31, 2011. The entire disclosure of Japanese Patent Application No. 2011-122158 is hereby incorporated herein by reference.

BACKGROUND

1. Technical Field

The present invention relates to an ultrasonic transducer that sends and/or receives ultrasonic waves, as well as a biological sensor equipped with said ultrasonic transducer, and a method for manufacturing said transducer.

2. Related Art

An ultrasonic transducer that sends and receives ultrasonic waves has been known before now (see Japanese Laid-Open Patent Application Publication No. 2003-304595, for example).

The diaphragm-type transducer (ultrasonic transducer) discussed in the above mentioned publication comprises a silicon substrate in which an opening is formed, an insulating layer and vibrating layer laminated on this substrate so as to block off this opening, and a piezoelectric element that is laminated over the vibrating layer and consists of a lower electrode, a piezoelectric thin-film, and an upper electrode. This ultrasonic transducer is formed by laminating the insulating layer, the vibrating layer, and the piezoelectric element on the upper side of the substrate, and then etching from the lower face of the substrate down to the insulating layer.

SUMMARY

With the ultrasonic transducer discussed in the above mentioned publication, a silicon substrate is used, and an opening is formed by etching down to the insulating layer from the lower side of the substrate. When a diaphragm is thus formed by etching a substrate, the thickness of the diaphragm may be uneven due to differences in the etching rate. Also, with a diaphragm is formed by etching, some of the silicon substrate may remain on the diaphragm if the etching duration is short, and over-etching may result in etching all the way down to the diaphragm if the etching lasts too long. If the diaphragm thickness thus ends up being uneven, there may also be variance in the drive characteristics of the ultrasonic transducer.

It is an object of the present invention to provide an ultrasonic transducer with stable drive characteristics, a biological sensor equipped with said ultrasonic transducer, and a method for manufacturing said ultrasonic transducer.

An ultrasonic transducer according to one aspect of the present invention includes a resin substrate, a support film and a piezoelectric element. The resin substrate has an opening. The support film blocks off the opening in the resin substrate. The piezoelectric element is disposed on the support film in a region that blocks off the opening in plan view from a thickness direction of the support film. The piezoelectric element includes a lamination of a lower electrode, a piezoelectric body, and an upper electrode.

The piezoelectric element here may be constituted such that it is provided directly on the surface of the support film, or may be provided with another layer in between.

With the above described aspect of the present invention, a support film is provided on a resin substrate, and a piezoelectric element is provided to the support film that blocks off the opening in the resin substrate. With an ultrasonic transducer thus constituted, the support film blocking the opening can be vibrated and ultrasonic waves generated by inputting a pulse signal to the piezoelectric element. Also, with this ultrasonic transducer, when the support film is vibrated by ultrasonic waves from the outside, an electrical signal corresponding to the vibrations can be outputted from the piezoelectric element, and an ultrasonic wave signal can be received.

With the above described aspect of the present invention, since the resin substrate is photosensitive, the resin substrate can be irradiated with light so as to modify the portion of the resin substrate that has been irradiated, and just the modified portion can be removed to form a cavity of easily and precisely.

Specifically, when an opening is formed by subjecting a substrate provided with a support film to etching with an inductively coupled plasma (ICP) or the like, for example, the portion that functions as the support film may also end up being etched away, and the thickness of the support film may be uneven. By contrast, with the present invention, the support film is not modified by optical irradiation, and just the photosensitive resin substrate that is irradiated with light is modified, so there is no change in the thickness of the support film in the formation of the opening, so the thickness can be more uniform.

Therefore, with the ultrasonic transducer of the present invention, the opening is blocked off by a support film having a uniform film thickness, and this means that the drive characteristics of the ultrasonic transducer will be stable.

With the ultrasonic transducer of the above described aspect of the present invention, the resin substrate is preferably a flexible photosensitive film.

With the above described aspect of the present invention, since the resin substrate is constituted by a photosensitive, the opening can be easily formed by irradiation with light as in the above-mentioned invention.

Also, since the photosensitive film is flexible, the shape of the photosensitive can be freely changed. Here, since the support film and the piezoelectric element send and receive ultrasonic waves as mentioned above, these members are formed on the film and are formed in a hardness that permits a certain amount of deformation. Therefore, the ultrasonic transducer of the above described aspect of the present invention constituted by this photosensitive film, support film, and piezoelectric element will also be flexible, and can be deformed into a planar shape that matches what is to be measured.

A biological sensor according to another aspect of the present invention includes a sensor main body in which a plurality of the above-mentioned ultrasonic transducers are provided, and a contact layer that touches the sensor main body and configured and arranged to come into close contact with an organism.

With the biological sensor of the above described aspects of the present invention, a plurality of the above-mentioned ultrasonic transducers are disposed on a sensor main body. As discussed above, the ultrasonic transducers have stable drive characteristics, and stable sending and receiving of ultrasonic waves is possible. Therefore, with a biological sensor equipped with such ultrasonic transducers, precise biological testing can be performed by accurately sending and receiving ultrasonic waves.

Also, if a flexible photosensitive film is used as the resin substrate, the sensor main body can be deformed to match the planar shape of the measurement object (such as the skin of an organism) when the sensor main body is brought into contact with the measurement object via a contact layer. Therefore, the biological sensor can fit more snugly against the organism, and more accurate biological testing can be performed.

A method for manufacturing an ultrasonic transducer according to another aspect of the present invention includes: forming a piezoelectric element by laminating a lower electrode, a piezoelectric body, and an upper electrode on a first face of a support film; affixing a reinforcing substrate that covers the piezoelectric element to the first face of the support film; forming a photosensitive resin substrate to a second face of the support film that is on an opposite side from the first face; forming an opening in the resin substrate by irradiating the resin substrate with light; and removing the reinforcing substrate. The photosensitive resin substrate here may be a positive-type photosensitive resin in which the photosensitive portion is dissolved, or a negative-type photosensitive resin in which the photosensitive portion remains and the non-photosensitive portion is dissolved.

With the above described aspect of the present invention, after the piezoelectric element has been formed on the first face of the support film in the piezoelectric element formation step, the resin substrate is formed on the second face of the support film in the resin substrate formation step, and the opening is formed in the resin substrate in the opening formation step. With an ultrasonic transducer formed by this manufacturing method, an opening can be formed easily and accurately, and an ultrasonic transducer with stable drive characteristics can be manufactured, by irradiating with light in the opening formation step.

Also, by affixing the reinforcing substrate to the support film, curving of the support film can be prevented in the formation of the resin substrate on the support film, or in the formation of the opening in the resin substrate, and the formation of the resin substrate and the opening can be carried out more accurately.

With the method of the above described aspect of the present invention for manufacturing an ultrasonic transducer, the forming of the resin substrate preferably includes affixing a flexible photosensitive film as the resin substrate to the second face of the support film.

With the above described aspect of this invention, just as with the aspect described above, because a flexible photosensitive film is used as the resin substrate, an ultrasonic transducer manufactured by this method will also be flexible. Therefore, the planar shape of the ultrasonic transducer can be freely modified to suit the intended use of the ultrasonic transducer.

The method of the above described aspect of the present invention for manufacturing an ultrasonic transducer preferably further includes forming the support film by forming a film member on one face of a substrate prior to the forming of the piezoelectric element, and adjusting a thickness of the support film to a prescribed film thickness by reducing a thickness of the substrate from an opposite side from a side of the substrate on which the film member is formed, prior to the forming of the resin substrate and after the affixing of the reinforcing substrate.

With the above described aspect of the present invention, the support film includes at least a film member formed in the film formation step, and the piezoelectric element formation step is carried out after this film member has been formed on the substrate. Therefore, in the formation of the piezoelectric element, there is no curving of the film member caused by the substrate, and the piezoelectric element can be formed accurately at the desired location.

Also, since the thickness of the substrate is adjusted by reducing the substrate by shaving, polishing, etc., after the reinforcing substrate affixing step, the support film can be formed in the desired thickness that suits the drive characteristics of the ultrasonic transducer.

With the method of the above described aspect of the present invention for manufacturing an ultrasonic transducer, the substrate is preferably opaque, and the adjusting of the thickness of the support film preferably includes forming the support film including the film member and a part of the substrate left behind after the reducing of the thickness of the substrate.

In the support film adjustment step, all of the film member may be removed by cutting, polishing, or otherwise working the substrate. However, if the film member is translucent, then when the photosensitive film is irradiated with light, the light that is transmitted by an $SiO_2$ layer may be reflected by the electrodes and so forth of the piezoelectric element and irradiate the photosensitive film again. If this happens, the reflected light may hit the side wall part of the opening, for example, so that the mask pattern used for form the opening has a different shape from that of the opening that is actually formed.

In contrast, with the above described aspect of the present invention, part of the opaque substrate is left behind and functions as part of the support film. With this constitution, since light is blocked by the remaining substrate, light is not transmitted to the piezoelectric element side, and the opening can be formed in the desired shape.

BRIEF DESCRIPTION OF THE DRAWINGS

Referring now to the attached drawings which form a part of this original disclosure:

FIG. 4 consists of cross sections of the ultrasonic transducer in the various steps in FIG. 3, with FIG. 4A being a cross section of after the piezoelectric element formation step, FIG. 4B a cross section in the reinforcing substrate affixing step, and FIG. 4C a cross section in the support film adjustment step;

DETAILED DESCRIPTION OF EXEMPLARY EMBODIMENTS

First Embodiment

A first embodiment of the present invention will now be described through reference to the drawings.

Configuration of Sensor Array

Figure 1:
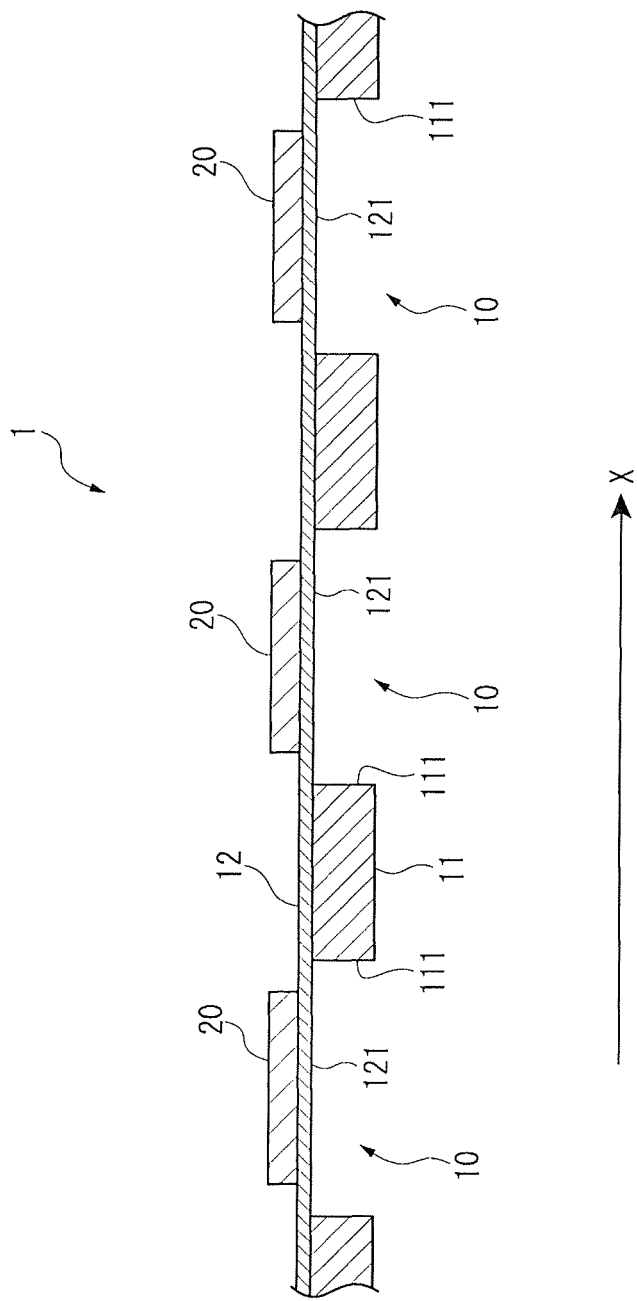
FIG. 1 is a cross section of the simplified configuration of a sensor array in an embodiment pertaining to the present invention.

FIG. 1 is a cross section of the simplified configuration of a sensor array comprising the ultrasonic transducer of the first embodiment of the present invention.

As shown in FIG. 1, a sensor array 1 comprises a plurality of ultrasonic transducers 10. In FIG. 1, an example is depicted in which the ultrasonic transducers 10 are arranged in just the X direction, but the ultrasonic transducers 10 may be arranged in a two-dimensional array along the X direction and the Y direction, for example.

Figure 2:
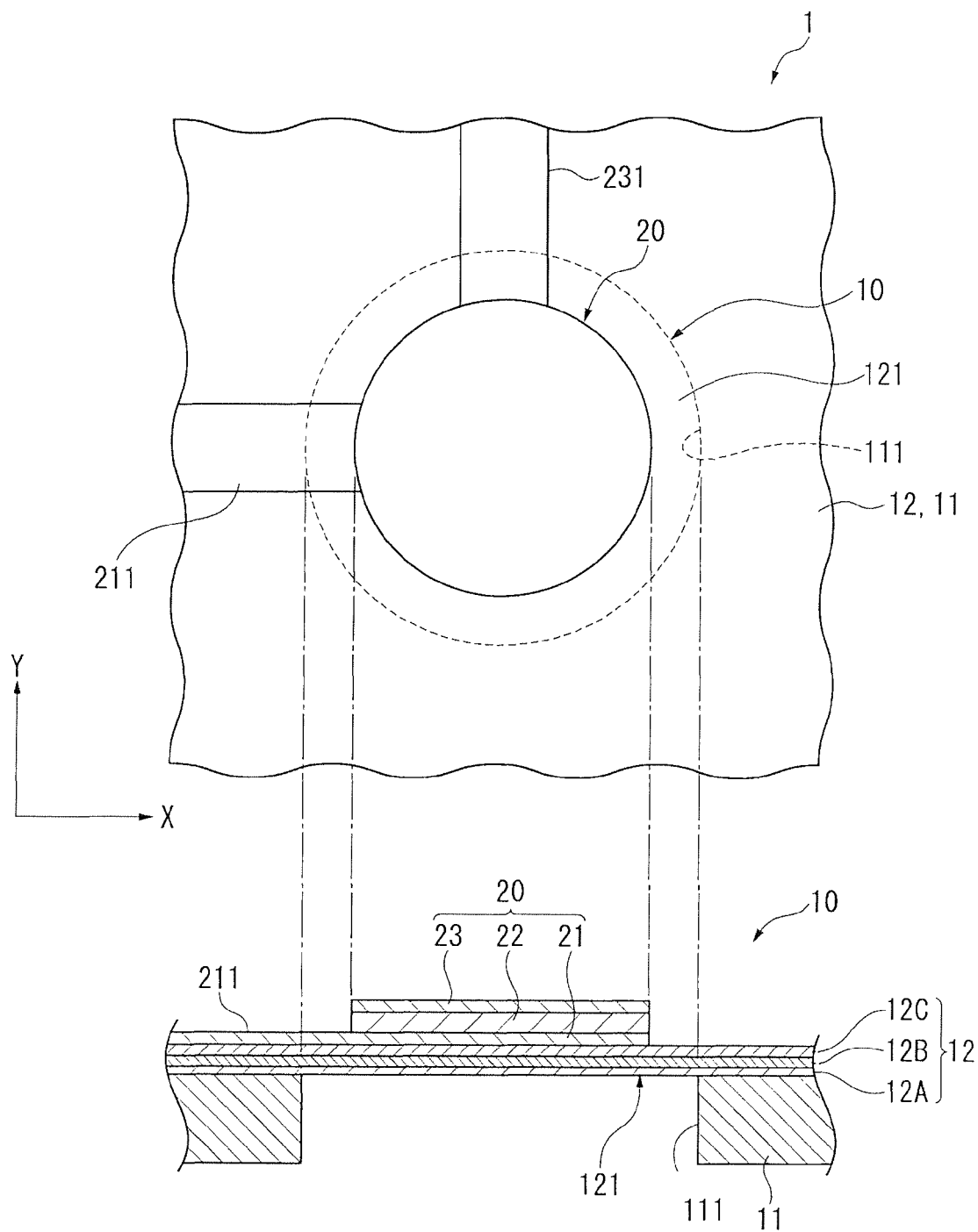
FIG. 2 is a plan view and a cross section of the simplified configuration of the ultrasonic transducer in a first embodiment.

FIG. 2 is a plan view and a cross section of the simplified configuration of one of the ultrasonic transducers 10. As shown in FIG. 2, The ultrasonic transducer 10 comprises a photosensitive film 11 (resin substrate) having an opening 111, a support film 12 formed on one side of the photosensitive film 11, and a piezoelectric element 20 foamed on the support film 12. This ultrasonic transducer 10 is a device that vibrates the support film 12 and outputs ultrasonic waves when voltage is applied to the piezoelectric element 20. An ultrasonic transducer that is used for generating ultrasonic waves is shown here, but this is not the only option, and the present invention can also be applied to an ultrasonic transducer that is used for receiving ultrasonic waves, in which the ultrasonic waves are received by the support film 12 and an electrical signal is outputted that corresponds to the vibrations from the piezoelectric element 20, or can be applied to an ultrasonic transducer capable of both sending and receiving ultrasonic waves.

Also, in this embodiment, only a single ultrasonic transducer 10 is shown, but in fact a plurality of the ultrasonic transducers 10 are laid out in an array to form an ultrasonic transducer group.

The photosensitive film 11 can be a photoresist that is sensitive to light of a specific wavelength (such as ultraviolet rays), and the photosensitive portion is modified. Also, if a positive photoresist is used as the photosensitive film 11, it is exposed at the location where the opening 111 is to be formed, and the portion degraded by this exposure is removed to form the opening 111. On the other hand, if a negative photoresist is used as the photosensitive film 11, everything but the location where the opening 111 is to be formed is exposed and cured, and the portion not exposed is removed to form the opening 111. In this embodiment, a positive photoresist is used as the photosensitive film 11.

The opening 111 formed in the photosensitive film 11 is preferably formed in a circular shape in plan view (sensor plan view) in which the photosensitive film 11 is seen in the thickness direction. Consequently, stress with respect to bending of a membrane 121 can be made uniform in the support film 12 (membrane 121) that blocks off the opening 111. The diameter of the opening 111 is suitably set according to the frequency of the ultrasonic waves generated from the ultrasonic transducer 10, with an example being a diameter of from 20 to 100 μm. In this embodiment, an example in which the opening 111 is circular in sensor plan view is depicted, but this is not the only option, and the opening may instead be formed as a slot (a rectangular shape).

The support film 12 is formed in a state of blocking off the opening 111 on the photosensitive film 11. This support film 12 has a three-layer structure consisting of a first support film 12A formed by a silicon layer that touches the photosensitive film 11, a second support film 12B formed by an $SiO_2$ film, and a third support film 12C formed by a $ZrO_2$ layer. The second support film 12B here can be formed by subjecting the substrate surface of the first support film 12A to thermal oxidation processing. The third support film 12C can be formed by sputtering zirconium or the like on the second support film 12B and then thermally oxidizing the film, or another such method. The $ZrO_2$ layer here is used to prevent the lead contained in the PZT from diffusing into the $SiO_2$ layer (the second support film 12B) when PZT, for example, is used as a piezoelectric layer 22 constituting the piezoelectric element 20. The $ZrO_2$ layer (the third support film 12C) also has the effect of improving bending efficiency with respect to distortion of the piezoelectric layer 22, for example.

The support film 12 comprises the membrane 121, which blocks off the opening 111.

The membrane 121 is a portion that is laminated with the piezoelectric element 20 and outputs ultrasonic waves by vibrating in the film thickness direction under drive by the piezoelectric element 20.

The piezoelectric element 20 is formed on the face of the membrane 121 of the support film 12 that is on the opposite side from the face touching the opening 111. This piezoelectric element 20 comprises a lower electrode layer 21, a piezoelectric layer 22, and an upper electrode layer 23.

The lower electrode layer 21 is formed in the inside region of the membrane 121 in sensor plan view, and the piezoelectric layer 22 is laminated to the upper layer. A lower electrode line 211 is connected from the outer peripheral edge of the lower electrode layer 21, and this lower electrode line 211 is connected to a lower electrode terminal (not shown) provided to the outer peripheral end edge of the support film 12.

The piezoelectric layer 22 is formed by being laminated over the lower electrode layer 21. This piezoelectric layer 22 is formed as a film of PZT (lead zirconate titanate), for example. PZT is used in this embodiment, but any material can be used as long as it is able to contract in the in-plane direction when voltage is applied. For instance, lead titanate ($PbTiO_3$), lead zirconate ($PbZrO_3$), lead lanthanum titanate ($(Pb, La)TiO_3$), or the like may be used.

This piezoelectric layer 22 expands and contracts in the in-plane direction when voltage is applied to the lower electrode layer 21 and the upper electrode layer 23. At this point, one face of the piezoelectric layer 22 is joined to the membrane 121 of the support film 12 via the lower electrode layer 21, while the upper electrode layer 23 is formed on the other face, but since no other layer is laminated over the upper electrode layer 23, the support film 12 side of the piezoelectric layer 22 is more resistant to expansion and contraction, while the upper electrode layer 23 side more readily expands and contracts. Accordingly, when voltage is applied to the piezoelectric layer 22, bending that becomes a bulge is created on the opening 111 side, and the membrane 121 is bent. Therefore, when AC voltage is applied to the piezoelectric layer 22, the membrane 121 vibrates with respect to the film thickness direction, and ultrasonic waves are outputted by this vibration of the membrane 121.

In sensor plan view, the upper electrode layer 23 is laminated over the piezoelectric layer 22 and patterned at a disposition location insulated from the lower electrode layer 21. Also, an upper electrode line 231 is connected from the outer peripheral edge of the upper electrode layer 23, and this upper electrode line 231 is connected to an upper electrode terminal provided to the outer peripheral end edge of the support film 12.

In driving the ultrasonic transducers 10, the lower electrode layer 21 may be grounded and a specific pulse drive signal inputted to the upper electrode layer 23. In this case, a lower electrode terminal may be provided to each of the lower electrode lines 211 of the various ultrasonic transducers 10, but in this case the layout of the electrode lines may become complicated in the sensor array 1. Therefore, the lower electrode lines 211 of the ultrasonic transducers 10 may be joined to a common electrode line, and this common electrode line connected to the lower electrode terminal. With a configuration such as this, fewer upper electrode lines 231 are needed and the sensor array 1 configuration can be simplified. The same applies when the upper electrode layer 23 is grounded and a specific pulse drive signal is inputted to the lower electrode layer 21. In this case, a plurality of upper electrode lines 231 can be joined to a common electrode line, and this common electrode line connected to the upper electrode terminal.

Also, in this embodiment a sensor array 1 used for generating ultrasonic waves was given as an example, but with a sensor array 1 used for receiving ultrasonic waves, the constitution may be such that a plurality of ultrasonic transducers 10 are electrically connected in series, for example, or such that the lower electrode line 211 of a single ultrasonic transducer 10 is connected to the upper electrode line 231 of the ultrasonic transducer 10 disposed adjacent to this first ultrasonic transducer 10. With a constitution such as this, ultrasonic wave reception sensitivity can be improved by adding current outputted from the ultrasonic transducers 10 during the receipt of ultrasonic waves.

Method for Manufacturing Ultrasonic Transducers

The method for manufacturing the above-mentioned ultrasonic transducers 10 will now be described through reference to the drawings.

Figure 3:
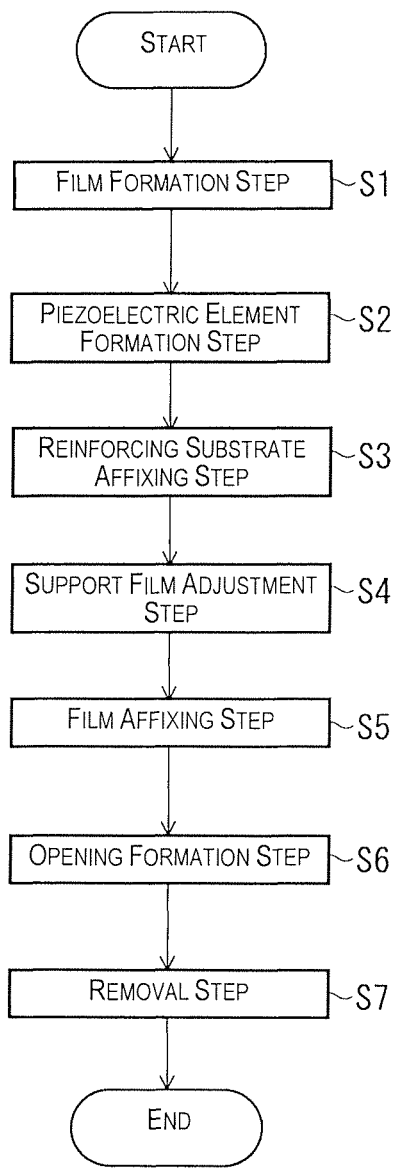
FIG. 3 is a flowchart of the method for manufacturing an ultrasonic transducer in the first embodiment.

FIG. 3 is a flowchart of the steps for manufacturing an ultrasonic transducer 10. FIGS. 4 and 5 are cross sections illustrating the state in each of the steps in FIG. 3.

To manufacture an ultrasonic transducer 10, first a silicon substrate 31 is subjected to a film formation step S1, for example.

In this film formation step S1, the substrate 31 undergoes thermal oxidation processing to form an $SiO_2$ layer (second support film 12B) on one side of the substrate 31. A zirconium layer is then formed by sputtering over this second support film 12B, and this zirconium layer is oxidized to form a third support film 12C.

In this embodiment the second support film 12B is formed by oxidizing the surface of the substrate 31, but the second support film 12B may be laminated and formed by sputtering or the like on the surface of the substrate 31.

After this, a piezoelectric element formation step S2 is performed. In this piezoelectric element formation step S2, first a conductive layer is uniformly formed over the first film surface 12D (constituting the first face of the support film in the present invention) of the third support film 12C by sputtering or the like, for example, and this product is then patterned by photolithography, for example, to form the lower electrode layer 21. There are no particular restrictions on the material of the conductive layer for forming the lower electrode layer 21, as long as it is electrically conductive, but in this embodiment a film with a laminated structure of Ti/Ir/Pt/Ti is used, and the film is formed in a thickness of 0.2 µm, for example, after firing of the piezoelectric layer.

After this, a film of PZT is formed over the third support film 12C and the lower electrode layer 21, and this film is patterned by photolithography, for example, to form the piezoelectric layer 22. The piezoelectric layer 22 is formed in a total film thickness of 1.4 µm, for example, using MOD (metal organic decomposition).

After this, a conductive film is formed uniformly by sputtering or the like over the third support film 12C, the lower electrode layer 21, and the piezoelectric layer 22, and the upper electrode layer 23 is formed by photolithography, for example. Just as with the lower electrode layer 21, the conductive film used to form the upper electrode layer 23 here may be any material that is electrically conductive. In this embodiment, an iridium film is used, and is formed in a thickness of 50 nm, for example.

As shown in FIG. 4A, the piezoelectric element 20 is thus formed over the third support film 12C.

After the piezoelectric element formation step S2, as shown in FIG. 4B, a reinforcing substrate affixing step S3 is performed in which a reinforcing substrate 32 is affixed so as to cover the piezoelectric element 20, over the support film 12 on which the piezoelectric element 20 of the third support film 12C has been formed. The reinforcing substrate 32 here comprises a glass substrate 321, a parting layer 322 stuck onto the surface of the glass substrate 321, and a resin layer 323 that is formed on the surface of the parting layer 322 and is affixed to the second support film 12B.

The glass substrate 321 here is a substrate that reinforces so that the support film 12 formed in a support film adjustment step S4 (discussed below) will not curve in a film affixing step (resin substrate formation step) S5 and an opening formation step S6, and is strong and thick enough to be able to support the support film 12. Also, the parting layer 322 is a layer that bonds the glass substrate 321 and the resin layer 323 together, and is formed, for example, from a material that can be easily broken by ultraviolet irradiation. The resin layer 323 is formed from a resin that can adhere to the third support film 12C and the piezoelectric element 20. For example, it is formed from a UV-curing resin or the like.

Next, the support film adjustment step S4 is carried out. In this support film adjustment step S4, the substrate 31 is cut or polished away from the face of the substrate 31 on which the reinforcing substrate 32 was affixed, thereby adjusting the thickness of the support film 12 as shown in FIG. 4C. More specifically, chemical mechanical polishing (CMP) is used to polish the substrate 31.

In this embodiment, the substrate 31 is not completely removed by cutting, and a very slight thickness of the substrate 31 is left behind to form the first support film 12A of the support film 12. The thickness of the first support film 12A should be sufficient to block the light in the optical irradiation performed in the opening formation step S6 (discussed below).

This support film adjustment step S4 results in the cut or polished face becoming a second film surface 12E that constitutes the second face of the support film of the present invention.

Figure 5A:
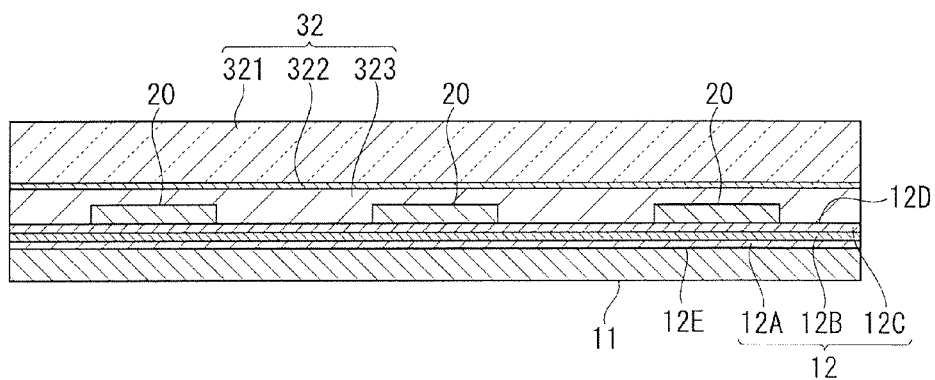
FIG. 5 consists of cross sections of the ultrasonic transducer in the various steps in FIG. 3, with FIG. 5A being a cross section in the film affixing step, and FIG. 5B a cross section in the opening formation step.

After the support film adjustment step S4, the film affixing step S5 is carried out. In this film affixing step S5, as shown in FIG. 5A, the photosensitive film 11 is affixed with a laminator to the second film surface 12E. In this embodiment, a positive photoresist is used as the photosensitive film 11, as mentioned above.

Figure 5B:
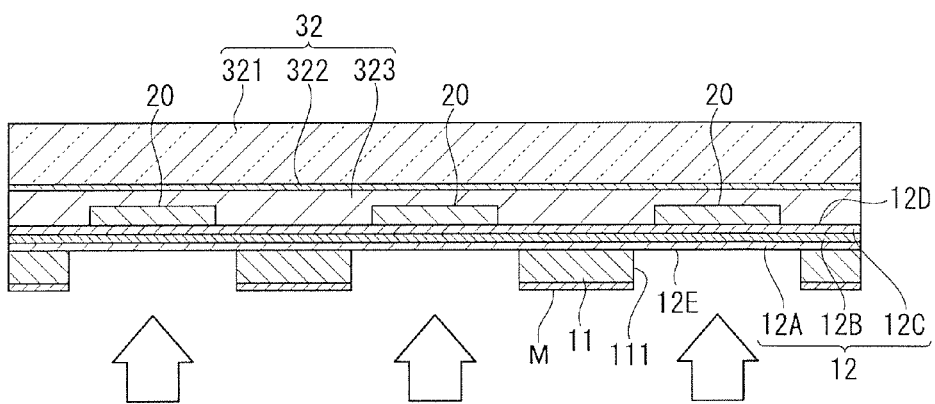

After the film affixing step S5, the opening formation step S6 is carried out to form the opening 111 as shown in FIG. 5B.

More specifically, in the opening formation step S6, first photolithography or the like is used to form a mask pattern M, which is open at the location where the opening 111 is to be formed, on the surface of the photosensitive film 11 affixed in the film affixing step S5. Light (such as ultraviolet rays) for degrading and removing the photosensitive film 11 is then directed in the parabolic direction of the surface of the photosensitive film 11. The portion of the photosensitive film 11 that has been photosensitively degraded is then dissolved away with a solvent, for example, to form the opening 111.

At this point, since the first support film 12A has been formed by part of the silicon substrate 31 in the support film adjustment step S4, the irradiating light is blocked by the first support film 12A, and does not pass to the second support film 12B or third support film 12C side, allowing the opening 111 to be formed accurately. That is, since the second support film 12B and the third support film 12C are translucent, if the irradiating light is transmitted in the opening formation step S6, the transmitted light will be reflected by the lower electrode layer 21, etc., of the piezoelectric element 20. Since the photosensitive film 11, the second support film 12B, and the third support film 12C each have a different refractive index, the reflected light is sometimes reflected in a direction that is inclined with respect to the parabolic direction of the photosensitive film 11. Also, the transmitted light is sometimes scattered by the piezoelectric element 20. If this reflected light is incident on the photosensitive film 11, the photosensitive film 11 will sometimes be removed from places masked by the mask pattern M, and the shape of the opening 111 (the planar shape of the membrane 121) will end up changing. In contrast, when the first support film 12A is formed, light used to form the opening 111 is not transmitted to the first film surface 12D side, so there is no degradation of the photosensitive film 11 by reflected light, and it is possible to form the opening 111 accurately at the desired location set by the mask pattern M.

After this, a removal step S7 is carried out to remove the mask pattern M and the reinforcing substrate 32. In this removal of the reinforcing substrate 32, a laser beam is directed from the glass substrate 321 side of the reinforcing substrate 32 to break the parting layer 322 and separate the glass substrate 321 from the resin layer 323. After this, the resin layer 323 and the mask pattern M are moved by being dissolved in a resist-removal solution, for example.

The sensor array 1 equipped with the ultrasonic transducer 10 shown in FIG. 1 is manufactured as above.

Action and Effect of First Embodiment

The following effects are obtained with the above ultrasonic transducer 10.

The ultrasonic transducer 10 in this embodiment comprises the photosensitive film 11 in which the opening 111 is formed, the support film 12 equipped with the membrane 121 that blocks off the opening 111 of the photosensitive film 11, and the piezoelectric element 20 provided on the membrane 121 of the support film 12. With this ultrasonic transducer 10, since the photosensitive film 11 is flexible, and the support film 12 is thick enough to vibrate the membrane 121, the structure is more pliant than when the support that supports the support film 12 is formed by a silicon substrate or another such semiconductor substrate. Therefore, the ultrasonic transducer 10 is flexible and can be freely deformed into a planar shape that matches the measurement object.

Also, in the manufacture of the ultrasonic transducer 10 having the photosensitive film 11, since the opening 111 is formed by irradiating the photosensitive film 11 with light in the opening formation step S6, the planar shape of the opening 111 and the thickness of the membrane 121 can be more accurate than when a silicon substrate or another such semiconductor substrate is etched, for example. That is, when a semiconductor substrate is etched, the etching rate varies from one spot to the next, and the etching duration is also difficult to control, so the membrane 121 will sometimes also be etched due to over-etching. If this happens, it is possible that the thickness of the membrane 121 will be uniform. In such a case, the vibration balance of the membrane 121 may be poor, the ultrasonic wave output may be low, and stable drive characteristics may not be obtained. Also, there is the risk that over-etching will result in etching all the way to the outside of the region where the opening 111 is supposed to be formed in plan view, and if this happens, it is possible that ultrasonic waves of the desired frequency cannot be generated from the membrane 121. In contrast, in this embodiment, the photosensitive film 11 is used as a member that supports the support film 12, and the opening 111 is formed by optical irradiation, so there is no problem with over-etching, and the membrane 121 can be formed in a uniform film thickness and in the desired region. Therefore, a high-quality ultrasonic transducer 10 with stable drive characteristics can be manufactured. Also, compared to when etching is performed using an ICP apparatus or the like, the opening 111 can be formed more easily by irradiation with ultraviolet rays or the like, the manufacturing cost can be lowered, and manufacturing efficiency can be improved.

Furthermore, with the ultrasonic transducer 10 having the photosensitive film 11, the photosensitive film 11 and the support film 12 can be easily integrated merely by affixing the photosensitive film 11 to the support film 12. The efficiency at which the ultrasonic transducer 10 is manufactured can therefore be increased.

In the manufacture of the ultrasonic transducer 10 in this embodiment, in the support film adjustment step S4 the support film 12 comprising the first support film 12A, the second support film 12B, and the third support film 12C is formed by cutting and polishing away all but part of the silicon substrate 31. With this constitution, even if the second support film 12B and the third support film 12C is translucent, since part of the opaque first support film 12A remains and makes up part of the support film 12, light is not transmitted from the support film 12 to the piezoelectric element 20 side in the opening formation step S6. Accordingly, this prevents the problem in which light transmitted by the support film 12 is reflected by the piezoelectric element 20 and is incident on the photosensitive film 11 outside of the location where the opening 111 is formed, and the opening 111 can be formed accurately at the desired location.

Second Embodiment

A second embodiment pertaining to the present invention will now be described through reference to the drawings.

In this embodiment, a biological test apparatus will be described as an example of an apparatus to which the ultrasonic transducer of the present invention is applied.

Configuration of Biological Test Apparatus

Figure 6A:
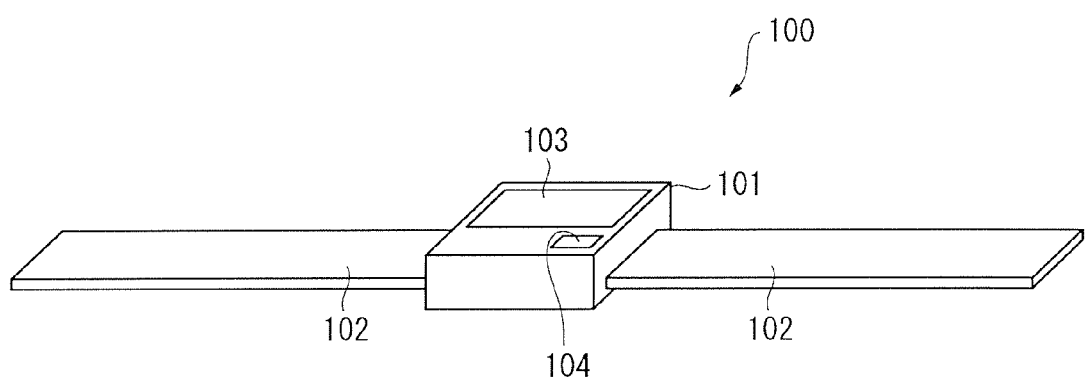
FIG. 6 consists of oblique views of the simplified configuration of a biological test apparatus in a second embodiment of the present invention, with FIG. 6A showing the front of this biological test apparatus, and FIG. 6B showing the rear of this biological test apparatus.
Figure 6B:
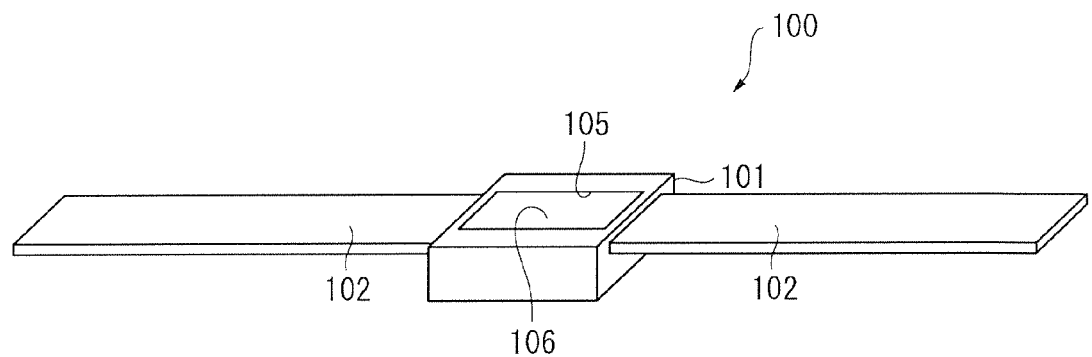

FIG. 6 consists of oblique views of the simplified configuration of the biological test apparatus in a second embodiment, with FIG. 6A showing the front of this biological test apparatus, and FIG. 6B showing the rear of this biological test apparatus.

In FIG. 6, a biological test apparatus 100 is used to measure the state of a vein, which is an organ in an organism, using ultrasonic waves. As shown in FIG. 6, this biological test apparatus 100 comprises an apparatus main body 101 and a band 102 that is connected to the apparatus main body 101. This biological test apparatus 100 is connected to an organism by placing its rear face against the organism and tightening the band 102, and the state of the vein can be monitored and measured for 24 hours, for example.

As shown in FIG. 6A, the front side of the apparatus main body 101 of the biological test apparatus 100 is provided with a display component 103 that shows measurement results, an interface 104 used to operate the biological test apparatus 100, and so forth. Also, a sensor window 105 is formed on the rear face side of the apparatus main body 101, and a biological sensor 106 equipped with the sensor array 1 of the first embodiment above is disposed in this sensor window 105. A measurement apparatus (not shown) that sends and receives signals to and from each of the ultrasonic transducers 10 and performs vein state testing on the basis of the received signals is provided inside the apparatus main body 101.

Figure 7A:
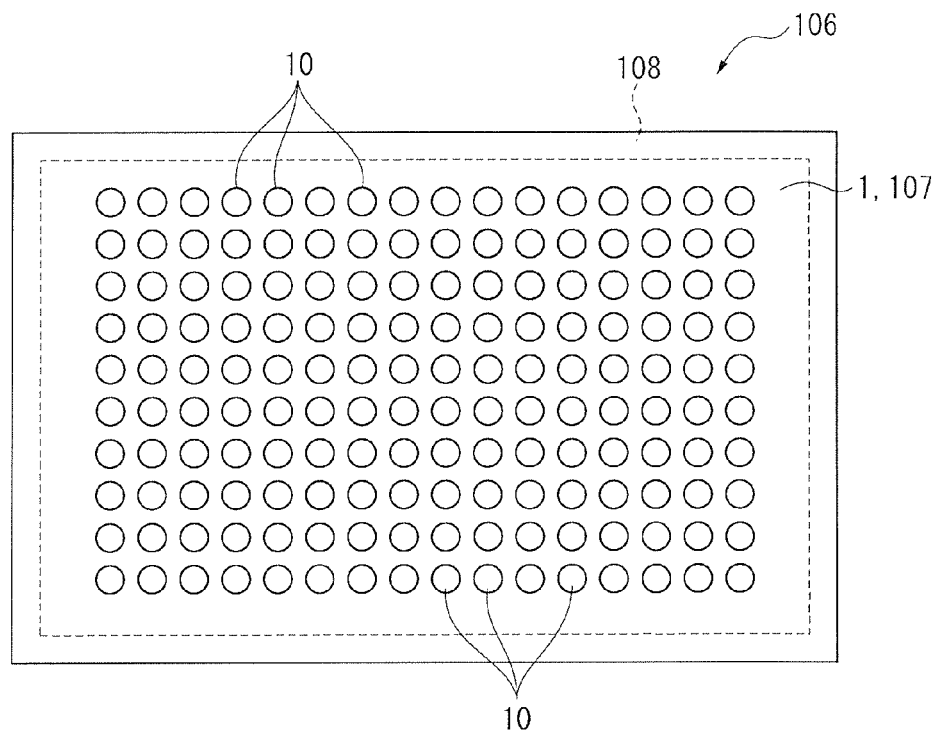
FIG. 7A is a plan view and FIG. 7B is a cross section of the simplified configuration of the biological test apparatus in the second embodiment.
Figure 7B:
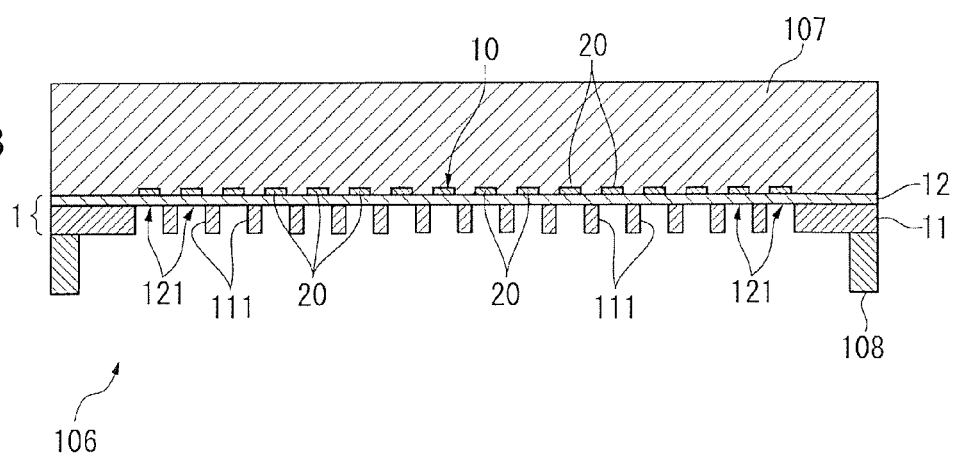

As shown in FIG. 7, the biological sensor 106 comprises the sensor array 1, a contact layer 107 provided on the front of the sensor array 1, and a reinforcing component 108 in the form of a frame that holds the sensor array 1.

The contact layer 107 fits snugly against the skin of the organism when the biological test apparatus 100 is brought into contact with the skin of the organism and fixed with the band 102. This contact layer 107 is formed from silicone rubber or another such material that has substantially the same acoustic impedance as the organism. The contact layer 107 also functions as a layer that protects the piezoelectric element 20 of the ultrasonic transducers 10 that make up the sensor array 1, as well as the lower electrode lines 211, the upper electrode lines 231, and other such wiring patterns against external pressure.

Also, as discussed above, since the sensor array 1 has as its base the flexible photosensitive film 11, its planar shape can be freely deformed. Therefore, when the contact layer 107 is fitted snugly against the organism, the planar shape of the sensor array 1 also deforms. Consequently, the distance between the ultrasonic transducers 10 and the organism can be kept substantially uniform, and this improves accuracy in biological testing.

The reinforcing component 108 is a frame-shaped member that holds the sensor array 1, and is fixed along the outer peripheral edge of the sensor array 1, for example. This prevents the sensor array 1 from being broken or otherwise damaged by excessive deformation.

The measurement apparatus controls the ultrasonic transducers 10 of the sensor array 1 and outputs ultrasonic waves from the ultrasonic transducers 10. When the ultrasonic transducers 10 receive ultrasonic waves reflected by a vein in the organism, the measurement apparatus acquires detection signals outputted from the ultrasonic transducers 10. The measurement apparatus then calculates the position of the vein, the speed of blood flow, the blood pressure, and so forth on the basis of how long it takes between the generation and the receipt of the ultrasonic waves.

Action and Effect of Second Embodiment

The biological sensor 106 of the above-mentioned biological test apparatus 100 comprises the sensor array 1 described in the first embodiment above, and the contact layer 107 provided on the support film 12 of the sensor array 1. Here, as discussed above, since the sensor array 1 is flexible and able to deform into any planar shape, when the contact layer 107 comes into contact with the skin of the organism and is elastically deformed, the planar shape of the sensor array 1 also deforms according to the deformation of the contact layer 107. Accordingly, the planar shape of the sensor array 1 is a shape that matches the skin of the organism. With a constitution such as this, since the distance between the ultrasonic transducers 10 and the skin is uniform, the time it takes for the ultrasonic waves generated from the ultrasonic transducers 10 to reach the organism is the same for all of the waves, and this reduces measurement error. Also, if the planar shape of the sensor array 1 did not change with respect to deformation of the contact layer 107, the stress applied from the contact layer 107 to the membrane 121 would concentrate in one part, and there would be the risk of diminished vibration of the membrane 121 at that location. In contrast, if the sensor array 1 deforms in response to deformation of the contact layer 107, stress from the contact layer 107 can be spread out evenly, and the membrane 121 can be vibrated favorably. Therefore, even if the biological test apparatus 100 is pressed against the measurement site on the organism in order to fit the biological sensor 106 snugly against the organism, the ultrasonic transducers 10 can still be driven stably.

Modification Examples

The present invention is not limited to the embodiments given above, and modifications, improvements, and so forth that still allow the object of the present invention to be achieved are encompassed by the present invention.

For instance, in the above embodiments, an example was given in which the flexible photosensitive film 11 was used as a resin substrate, but this is not the only option. In application to the biological sensor in the second embodiment, for example, it is preferable if the photosensitive film 11 is flexible so as to deform the sensor array 1 according to the measurement position on the organism, but as long as the planar shape of the sensor array 1 is fixed, a resin substrate with greater hardness may be used.

Also, in the above embodiments, in the opening formation step S6 a positive photosensitive resin was used as the photosensitive film 11, and the location where the opening 111 was to be formed was irradiated with ultraviolet rays to remove the photosensitive portion, but this is not the only option. For example, a negative photosensitive resin may be used as the photosensitive film 11. In this case, the location where the opening 111 is to be formed is covered with a mask, the photosensitive portion is modified and affixed, and the portion that is not photosensitive is removed with a developer solution to form the opening 111. An example of such a negative photosensitive resin is a MEMS-use permanent photoresist (trade name: TMMF S2000, made by Tokyo Ohka Kogyo).

Also, in the first embodiment above, part of the substrate 31 was left behind as the first support film 12A in the support film adjustment step S4 in order to prevent light from being transmitted to the first film surface 12D side in the opening formation step S6, but if, for example, an opaque film member is formed in the film formation step S1, all of the substrate 31 may be removed by cutting or the like in the support film adjustment step S4. Also, the support film 12 may be constituted by just one sensor array layer, or by two layers, or by four or more layers of film member.

The biological sensor 106 that was incorporated into the biological test apparatus 100 for detecting the state of a vein as discussed in the second embodiment was given as an application example of the ultrasonic transducers 10 of the present invention, but this is not the only option. For example, the ultrasonic transducer of the present invention may be used as a biological sensor in a biological test apparatus for testing the liver or other such organs. Application is not limited to a biological sensor, either, and the present invention can also be applied to any apparatus that generates and/or receives ultrasonic waves, such as a washing apparatus for washing something with ultrasonic waves, or an object detection sensor that tests the position of an object with ultrasonic waves.

Preferred constitutions for working the present invention were described in specific terms above, but the present invention is not limited to these. Specifically, the present invention is particularly depicted and described mainly in relation to specific embodiments, but a person skilled in the art can add various modifications and improvements to the embodiments given above, without departing from the scope of the object or the technological concept of the present invention.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:
1. An ultrasonic transducer comprising:
a resin substrate having an opening;
a support film that blocks off the opening in the resin substrate; and
a piezoelectric element disposed on the support film in a region that blocks off the opening in plan view from a thickness direction of the support film, the piezoelectric element including a lamination of a lower electrode, a piezoelectric body, and an upper electrode.
2. The ultrasonic transducer according to claim 1, wherein the resin substrate is a flexible photosensitive film.
3. The ultrasonic transducer according to claim 1, wherein the resin substrate further has a plurality of additional openings,
the support film blocks off the additional openings, and
the ultrasonic transducer further includes a plurality of additional piezoelectric elements disposed on the support film respectively in regions that block off the additional openings in plan view from the thickness direction of the support film, each of the additional piezoelectric elements including a lamination of a lower electrode, a piezoelectric body, and an upper electrode.
4. A biological sensor comprising:
a sensor main body including a plurality of the ultrasonic transducers according to claim 1; and
a contact layer that touches the sensor main body, and configured and arranged to come into close contact with an organism.
5. A biological sensor comprising:
a sensor main body including the ultrasonic transducer according to claim 3; and
a contact layer that touches the sensor main body and configured and arranged to come into close contact with an organism.

* * * * *